United States Patent
Schmitz et al.

(10) Patent No.: US 6,186,006 B1
(45) Date of Patent: Feb. 13, 2001

(54) METHOD FOR THREE-DIMENSIONAL AND NON-DESTRUCTIVE DETECTION OF STRUCTURES

(75) Inventors: Volker Schmitz, Dudweiler; Herbert Wiggen-Hauser, Berlin; Martin Krause, Berlin; Christiane Maierhofer, Berlin, all of (DE)

(73) Assignee: Fraunhofer-Gesellschaft zur Foerderung der Angewandten Forschung e.V., Munich (DE)

( * ) Notice: Under 35 U.S.C. 154(b), the term of this patent shall be extended for 0 days.

(21) Appl. No.: 09/214,829
(22) PCT Filed: Aug. 12, 1997
(86) PCT No.: PCT/EP97/04371
§ 371 Date: Jan. 13, 1999
§ 102(e) Date: Jan. 13, 1999
(87) PCT Pub. No.: WO98/08111
PCT Pub. Date: Feb. 26, 1998

(30) Foreign Application Priority Data

Aug. 22, 1996 (DE) .............................................. 196 33 813

(51) Int. Cl.$^7$ .................................................... G01N 29/18
(52) U.S. Cl. .............................. 73/598; 73/598; 342/179; 367/13; 324/344
(58) Field of Search ............................ 73/597, 598, 602, 73/618, 619, 620; 342/25, 179, 165, 174; 367/13; 324/344

(56) References Cited

U.S. PATENT DOCUMENTS

| 5,495,576 | * | 2/1996 | Ritchey | 395/125 |
| 5,805,098 | * | 9/1998 | McCorkle | 342/25 |

FOREIGN PATENT DOCUMENTS

| 61791 | * | 4/1984 | (JP) . |
| 201382 | * | 9/1987 | (JP) . |
| 242186 | * | 8/1992 | (JP) . |

* cited by examiner

Primary Examiner—Hezron Williams
Assistant Examiner—Nashmiya Fayyaz
(74) Attorney, Agent, or Firm—Evenson, McKeown, Edwards & Lenahan, P.L.L.C.

(57) ABSTRACT

A method for nondestructive, three-dimensional detection of structural elements in structures, especially those made of concrete or similar materials, allows an area to be investigated to be scanned areawise using ultrasound and by recording high-frequency, travel-time-dependent data for the individual points. In an imaging method, the respective volume image of the area being investigated is determined. This method is improved in such fashion that the accuracy of the location of structures is improved. It is proposed that the area to be investigated be scanned by both ultrasound and radar and that a structural representation of the area investigated be performed both on the basis of data acquired using sound and on the basis of data acquired using radar, with these two representations being calibrated.

21 Claims, 4 Drawing Sheets

METHOD FOR THREE-DIMENSIONAL AND NON-DESTRUCTIVE DETECTION OF STRUCTURES

BACKGROUND OF THE INVENTION

The invention relates to a method for nondestructive, three-dimensional detection of structural elements in structures, especially those made of concrete or similar materials.

A method of this kind is known from DE-A-43 20 473 according to which the echo signals from the far field of a single ultrasonic test head can be detected. The amplitudes and travel times of the echo signals can be stored together with the position of the ultrasonic test head in a memory unit as travel time-location curves with the corresponding amplitude values. From the totality of the travel time-location curves, by means of a filter device that has an image-producing device located upstream of it, selectable portions of the stored location curves can be filtered out.

In ultrasonic test methods, sound waves are regularly emitted in the lower frequency range and the multiple reflections of sound waves between a transmitting and/or receiving point and the object to be measured are utilized as the measured parameter. This produces significant peaks in frequency graphs from which the distance to the object can be calculated, if the speed of the waves is known. In the publication "Schickert, G. (editor): Papers and Reports of the International Symposium on Nondestructive Testing in Construction, Report Volume 21, Berlin: DGZfP 1991, pp. 488–504; Wüstenberg H., Possibilities and Concepts for Ultrasonic Test Heads, Especially for Construction," regarding the use of ultrasonic echo methods on structures made of concrete, the use of an artificial aperture was proposed. The goal is to eliminate the problems that result from the use of large-area ultrasonic heads by moving small comparatively simply constructed test heads and processing the signals accordingly. For this purpose, an illuminating test head was coupled to the underside of a concrete block and a shadow caused by refraction was produced by means of a bore. As a result of numerical storage of the sound signals recorded with amplitude and phase and of reconstruction using the algorithms of holography, the approximate size of the disturbing object could be determined. However, it is disadvantageous that significant phase errors can be produced due to the non-constant coupling, so that evaluation based on phase-sensitive scanning is unreliable.

In addition, electromagnetic radar methods are employed based on the idea that layers with different dielectric properties are present in the material to be tested. A method of this kind is known from the publication "Symposium on Nondestructive Testing in Construction, Feb. 27, 1991 to Mar. 1, 1991 in Berlin, Report Volume 21, Part 2, pp. 537–544; Author: Dipl.-Ing. C. Florher, Hochtief, Frankfurt/Main; Dipl.-Ing. B. Bernhardt, Berlin, The Locations of Stress Reinforcements Beneath Multilayer Reinforced Concrete Reinforcements." Using an antenna, pulses were transmitted and received primarily in the frequency range between 900 MHz and 2 GHz. The depth information was obtained from the travel-time measurement of the reflected signals, with the propagation rate being calculated from the speed of light in a vacuum divided by the root of the average dielectric constant of the material being investigated. Typical values for the dielectric constant for example are 7 for concrete, 4 for brick, 81 for water, and infinity for iron. Since the value of the dielectric constant is also dependent on moisture, evaluation requires an expert and experienced specialist. In the radar method an antenna is moved continuously, and accordingly a manipulator is used in the ultrasonic test method that is based on the principle of the synthetic aperture. On the basis of these common features, a depth-dependent representation of the object under investigation is made possible by arranging the recorded amplitudes in series. From the different travel times of the signals as well as the dielectric constants of the materials, the depth position of the imaged object is estimated, but the accuracy of the location depends largely on the moisture content of the material or on cavities filled with water, among other factors.

In addition, from the publication "Acoustical Imaging, Vol. 19, edited by Helmut Ermert and Hans-Peter Harjes, Plenum Press, New York and London; Authors: Schmitz, V.; Müller W.; Schafer G.; Synthetic Aperture Focusing Technique—State of the Art" an imaging method is known called "synthetic aperture focusing technique, or SAFT. This imaging method makes it possible to calculate the respective spatial image of an area under investigation.

Finally, a method for measuring the thickness of dielectric objects is known from SU-A-1 364 868. According to this method, electromagnetic waves and sound waves are directed alternatively at the object and the thickness of the object is calculated as a function of the reflected energy.

SUMMARY OF THE INVENTION

Taking its departure from this technology, the goal of the invention is to improve the method of the species recited at the outset in such fashion that the accuracy of the location of structures is improved. The results will largely be independent of ambient variables and boundary conditions. Furthermore, the method can be implemented at an cost that is as low as possible.

The method according to the invention for nondestructive three-dimensional detection of structural elements is used primarily for testing structures and monitoring structures. It permits optimum determination of the thickness of walls and foundations or of cavities in prestressing cuts. Furthermore, the exact position of prestressing elements, prestressing cuts, and other structural elements can be determined. In addition, with the method according to the invention, the location and classification of material inhomogeneities can advantageously be performed. especially the fine cracks caused by corrosion of reinforcing rods.

Using the method according to the invention, the area to be investigated is scanned areawise both by radar and sound, with the high-frequency travel-time dependent data being recorded at each point. By means of an ultrasonic imaging method, especially the synthetic aperture focusing technique, hereinafter called SAFT, which is a three-dimensional method, an image of a common volume range is generated. Optionally, any layer thicknesses and optionally these same layers in any direction can be displayed. These layers can be shown both parallel to the measured surface and also perpendicular to the measured surface. Advantageously, local calibration of the respective volume ranges is performed with the aid of "fingerprints." Moreover, in volume reconstruction using the special integration method described, the signal/noise ratio is improved. The data are linked with one another in any sectional planes desired, and a quantitative analysis of the volume range is performed on the basis of the precisely located link. In this way, unknown materials can be identified from a knowledge of dielectric constants and moisture distribution.

BRIEF DESCRIPTION OF THE DRAWINGS

The invention will now be described with reference to the drawing and special embodiments, without the invention being limited to said embodiments.

DETAILED DESCRIPTION OF PREFERRED EMBODIMENTS

Figure 1:
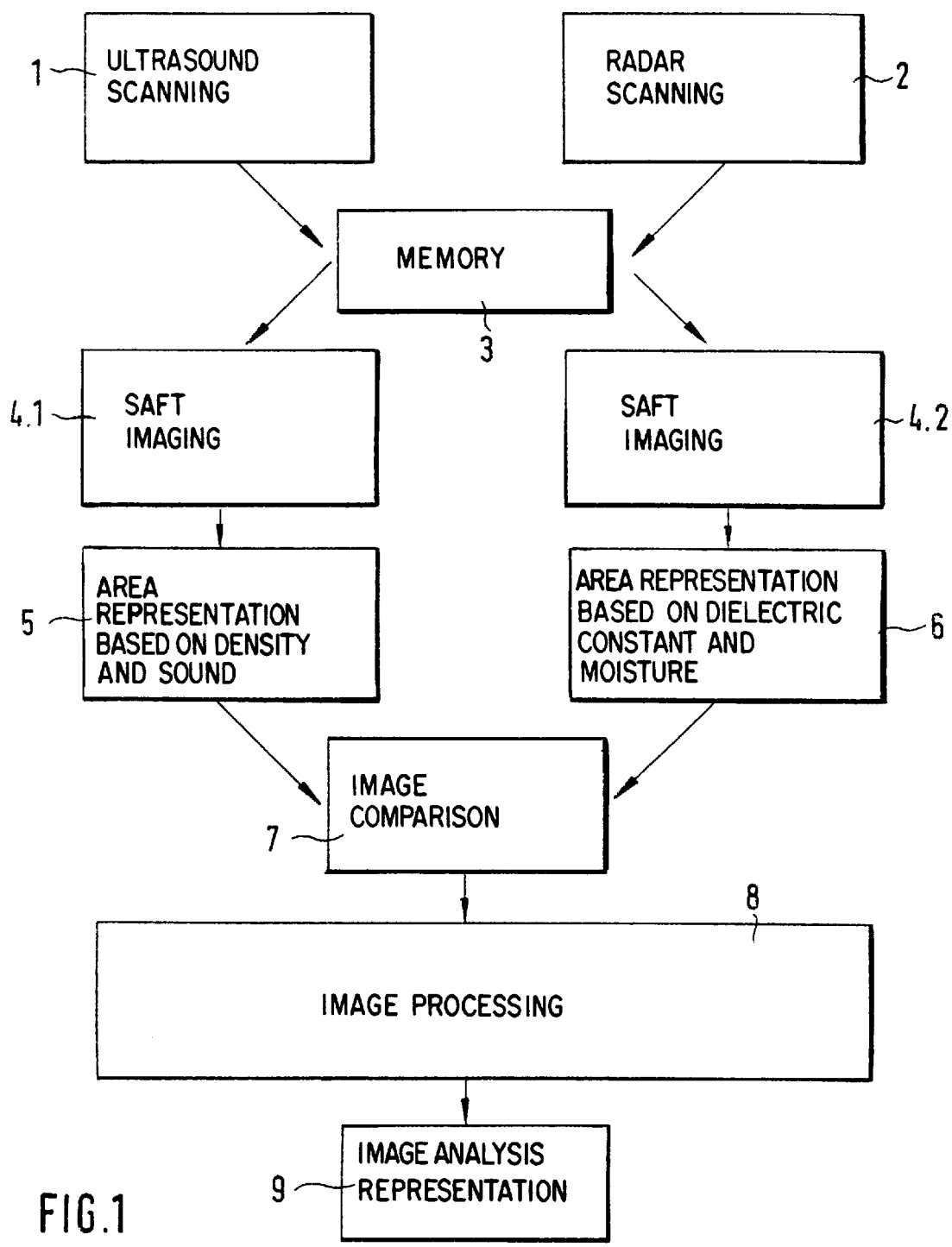
FIG. 1 is a flowchart to explain the basic method steps.

The basic process involved in the method will now be described in greater detail with reference to FIG. 1, with the individual functional blocks having the following functions. The surface of the part to be tested is scanned areawise and, in accordance with block 1, scanning using ultrasound is performed first. In a second step, the ultrasonic sensor is replaced by a radar antenna according to block 2. The radar antenna is likewise moved in a scanning pattern and picks up signals from the same volume range beneath the area being scanned. The signals thus detected are high-frequency signals per location of the respective sensor, whose amplitudes depend on the respective ground structure and its shape over time from the distance of the respective structure from the surface. All of the time-dependent signals detected in method steps 1 and 2 are entered into a memory 3 and stored.

From the stored data, in the imaging method according to blocks 4.1 and 4.2, especially in accordance with the "synthetic aperture focusing technique—SAFT," the respective spatial image of the investigated area is determined, as will be explained in greater detail below. It is expressly provided that no two-dimensional sectional planes are imaged from the volume area under investigation, but a three-dimensional volume is calculated for each of the two method components, sound and ground radar. It is important in this connection that in accordance with block 5 the structural representation of the area under investigation by means of sound is based on density and sound speed differences and that according to block 6 the structural representation of the area under investigation by means of ground radar depends on the dielectric constant and consequently on the moisture distribution as well. In a step that is important to the invention, a depth-dependent calibration of the images on the two method pathways is performed. According to block 7, therefore, an image comparison and a scale calibration are performed on the basis of local fingerprints. It has been observed that in three-dimensional imaging, structures are present that can be identified by the two imaging methods independently of one another. These structures, detected by both of the two method components, which are called fingerprints, are used in an especially advantageous manner for adjusting the scales of the two images to one another according to the invention.

It should be noted that in geological investigations, it is primarily sectional planes imaged perpendicularly to the surface that are regularly represented as the y-z plane. With the method proposed according to the invention it is now possible in data acquisition using both ultrasound and ground radar to seek out sectional planes in any planes and to link the imagewise representation of the ground structures by image processing as indicated in functional block 8. In image processing, the imaging structures can be shown optimized by ANDing, ORing, peak formation, or other methods. Advantageously, the representation follows the ground structure. If the horizontal structural change is of interest, a horizontal layer in a thickness range that can be specified is selected from the reconstructed volume range. If interesting conclusions regarding the vertical pattern result from this, corresponding vertical layer thickness planes can be selected according to the invention. Moreover, it is also possible within the scope of the invention to view the investigated volume range in perspective at any desired spatial angle.

After a representation has been assured that is true to scale and the part structure has been represented optimally, analysis is performed according to block 9. This is based on identification of areas of increased sound reflection as well as identification of areas with different dielectric constants. As a result of the interaction of the two physical parameters, it becomes possible according to the invention, for example by scale relationship, to determine the local dielectric constant and from this the moisture of the investigated ground area. In addition, unknown dielectric constants can be determined by calibrating the image, which is performed on the basis of ultrasonic measurement, in order to draw conclusions from this about unknown materials.

Figure 2:
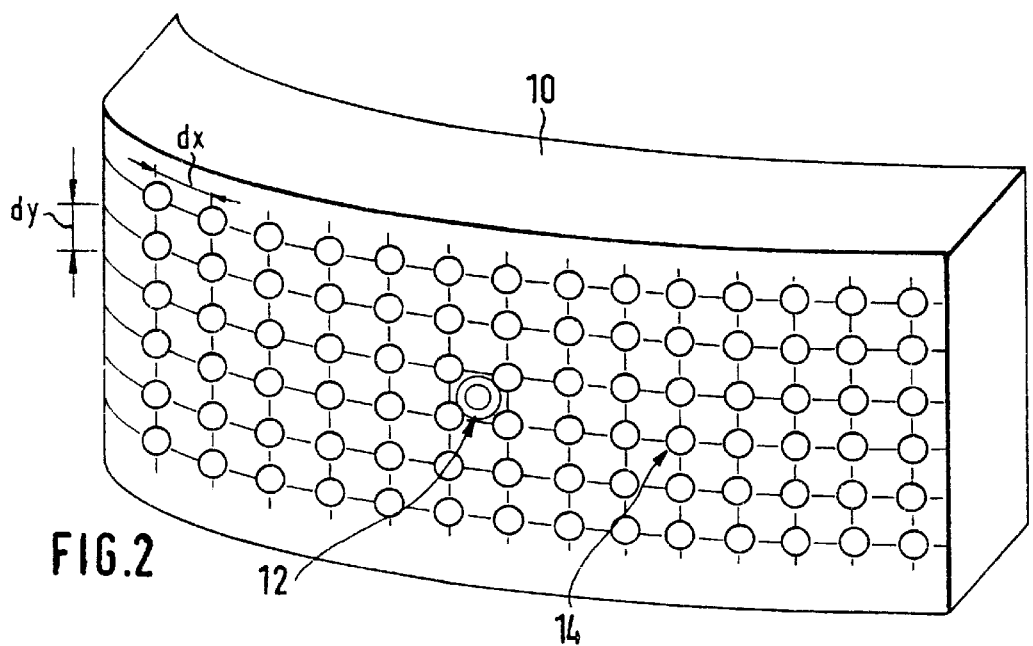
FIG. 2 is a schematic diagram explaining data acquisition using ultrasound.

With reference to FIG. 2, the test techniques used for data acquisition by means of ultrasound in accordance with functional block 1, in FIG. 1, will be explained. As is known, in test head coupling on structural elements made of stone or concrete, problems occur because of the surface roughness of the material. Therefore it is not unusual to use mortar to couple a test head in place. This is done with a single test head 10 designed as a transmitter. By means of test head 10, the sound is transmitted but not received. Reception of the reflected signals at the various surface points is accomplished by scanning the corresponding positions using a laser beam. The scanning intervals are specified as a function of the requirements, and 2×2 cm and 5×5 cm for example have proven to be advantageous as typical scanning intervals.

Figure 3:
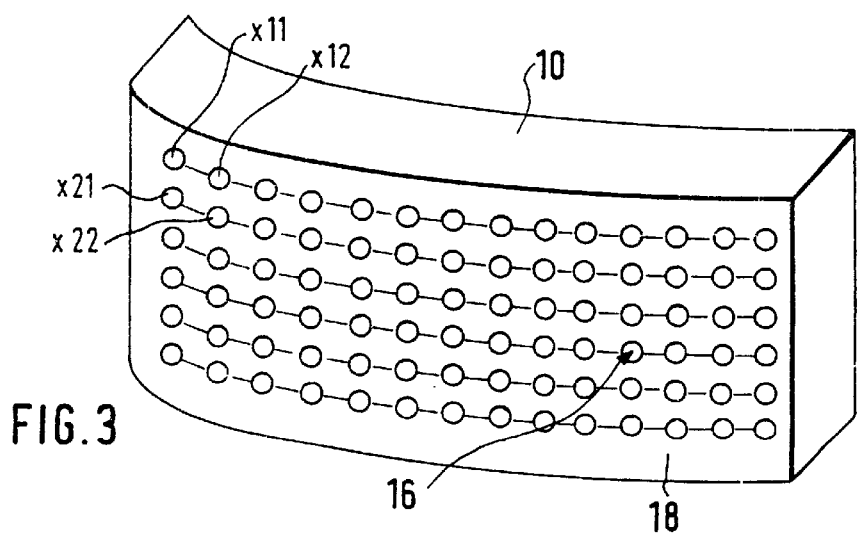
FIG. 3 is a version for data acquisition using ultrasound.

In the embodiment according to FIG. 3, scanning is performed by an ultrasonic test head 12 that can both transmit and receive sound. This takes place at specified positions in a first row, in other words at points x11, x12, . . . , a second row, therefore x21, x22, . . . , etc. of concrete wall 10. In order to solve the problems of coupling to surface 18, the method uses contact technology.

Figure 4:
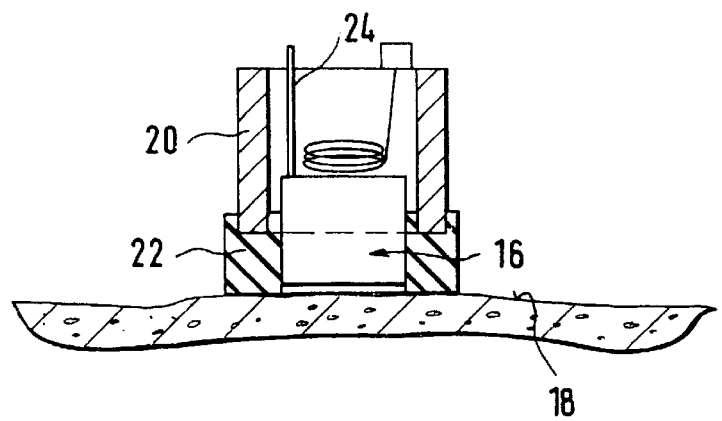
FIG. 4 is a schematic diagram showing the parts of a test head.

As shown in FIG. 4, combined test head 16 is located in a housing 20 that is sealed off from concrete surface 18 by means of a ring 22, especially a ring made of rubber or Styropor combined with grease. Liquid, preferably water, is supplied through suitable channels and carried away through hoses 24, with only the liquid/water that is lost as a result of surface roughness and the absorbency of the ground having to be replaced. Advantageously, a circulating system is provided, with the liquid or water being filtered during every passage.

Figure 5:
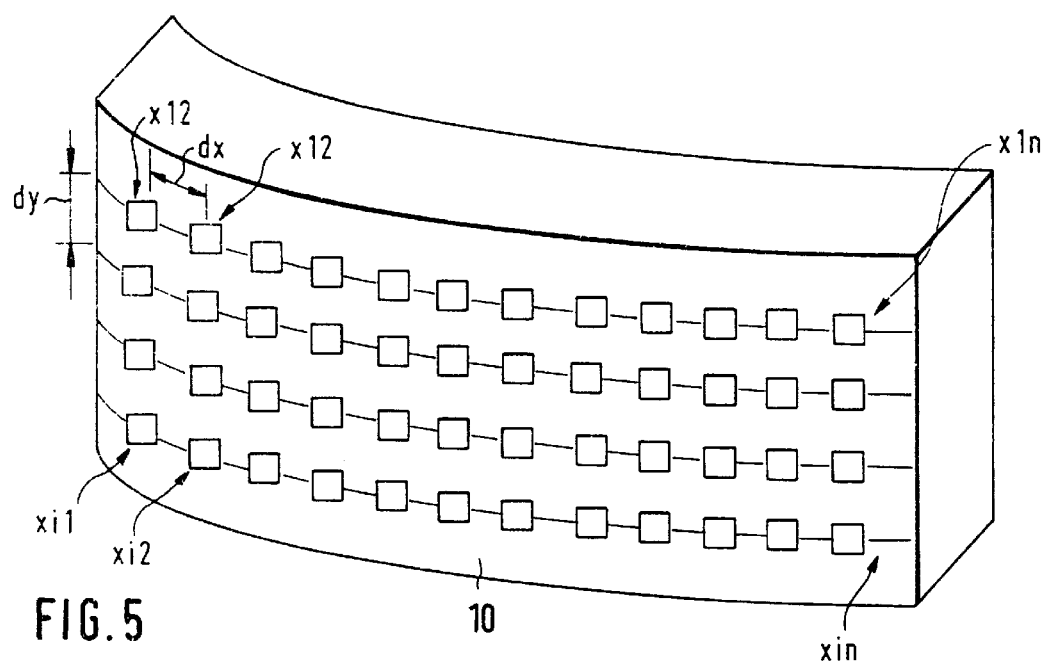
FIG. 5 is a schematic view showing the system for data acquisition using ground radar.

The scanning of the wall using ground radar will now be described in greater detail with reference to FIG. 5. Likewise, location-dependent transmission of signals as well as their reception is performed by scanning the wall and/or structure. Scanning using ground radar can in fact be performed advantageously at the same positions as scanning with ultrasound, but this is not a necessary condition. For different scanning positions, the relative positions of all the scanning points with respect to one another are also recorded and/or stored.

Figure 6:
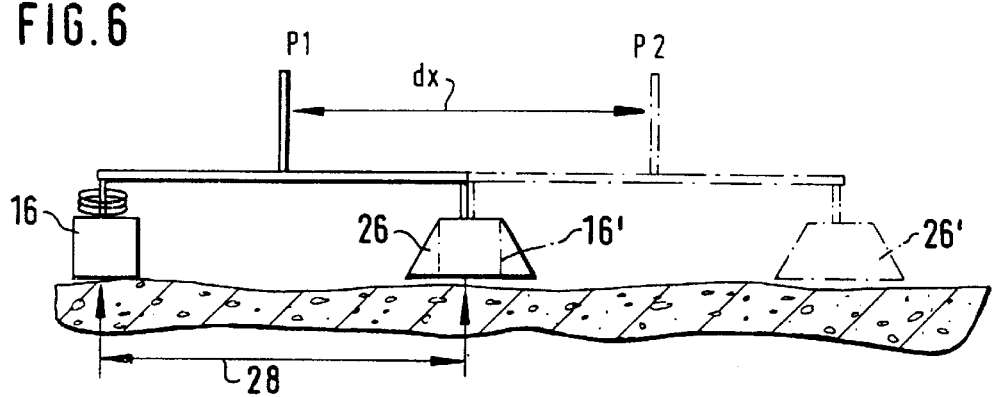
FIG. 6 shows a combined system composed of an ultrasonic test head and a radar antenna.

In an especially advantageous embodiment, a combined sensor technique according to FIG. 6 is used in an advantageous manner to save time during data acquisition. In this case, the method steps explained with reference to FIGS. 4 and 5 are used. According to the invention, the distance of the radar and sound sensors is specified in such fashion that it corresponds to the scanning distance dx multiplied by a whole-number factor equal to or larger than 1. As a result, assurance is automatically provided that the acoustic irradiation locations match identically from one test shot to the next test shot for the selected sensors. In position P1, the ultrasonic test head 16 and radar antenna 26 are represented by solid lines. The ultrasonic test head 16 and radar antenna 26 are shown at a distance 28 from one another. In the next position P2, indicated by dashed lines, the ultrasonic test head is displaced by a distance dx. Since the respective distances dx of the measured points corresponding to positions P1 and P2 according to the invention correspond to the distance 28 between the sensors, the ultrasonic test head is at the same location in position P2 as the radar antenna was in point P1.

Figure 7:
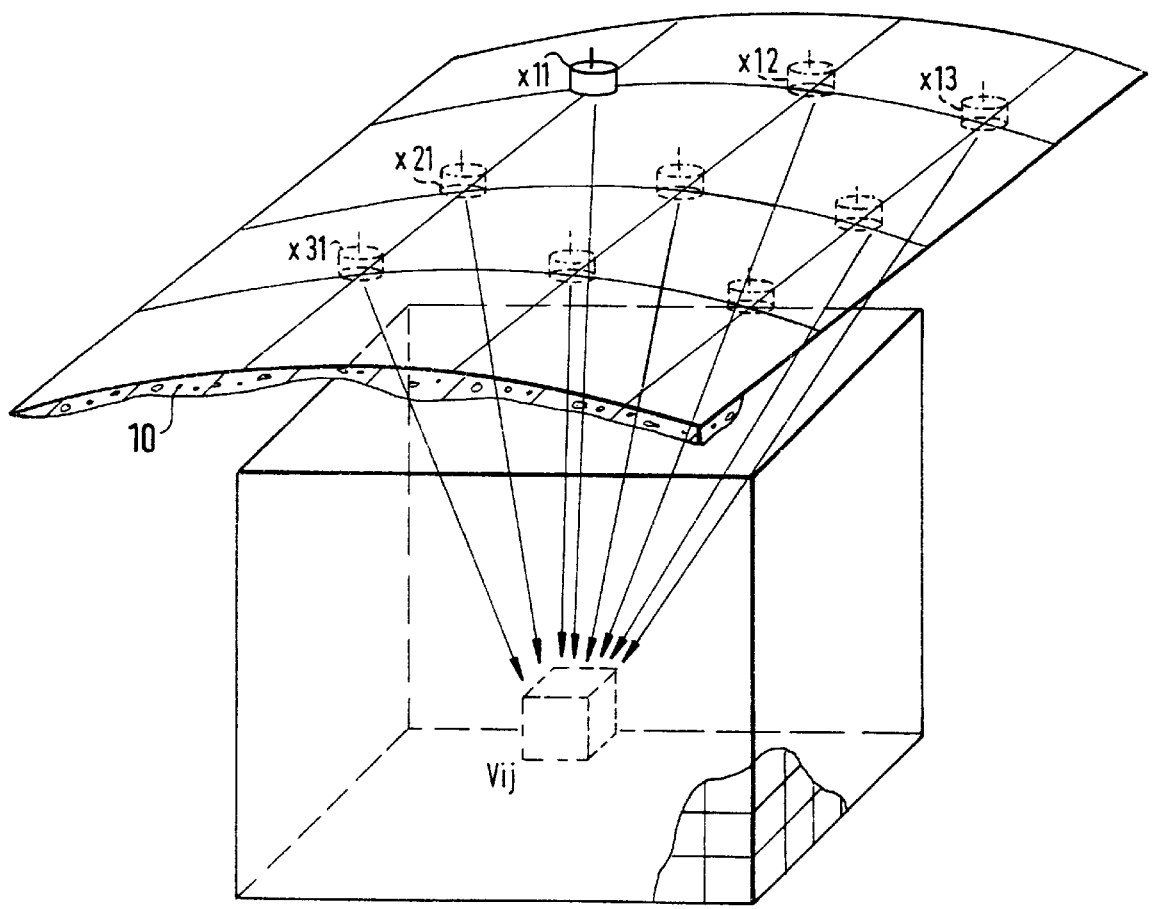
FIG. 7 is a schematic view of image generation.

The three-dimensional image generation of the imaging method corresponding to functional blocks 4.1 and 4.2 in FIG. 1 will now be described in greater detail with reference to FIG. 7. Advantageously, the three-dimensional reconstruction is performed using the principle of the three-dimensional "synthetic aperture." At points x11, x12, . . . the measurement data, preferably high-frequency ultrasound and radar data, are stored. The material range to be investigated/imaged is broken up into small volume cells. Typical orders of magnitude are in the millimeter and centimeter ranges. The distance from the measurement points to the volume cells is calculated. The distance for the ground radar is converted into travel time using the speed of light and the dielectric constant $\in$. In addition, by using the speed of sound and the density, the distance for the ground wave is likewise converted into travel times. Thus, by using the amplitude values recorded as a function of time, allocation to the affected volume cells can be performed depending on the position. The amplitudes associated with the calculated travel times are stored or assigned to the volume cells. The information collected for all the measurement points is summed in the volume cells, corrected for travel time. Then the video signal for the display is formed from the investigated volume range. Thus, from the amplitude values stored as a function of travel time, position-dependent allocation to the affected volume cells is performed. This method is especially advantageous for the frequency range used for concrete, which in particular is between 50 KHz [sic], with the test heads radiating sound in angle ranges advantageously up to +/−90°.

By means of the SAFT method used according to the invention, it is possible largely to suppress the influence of surface waves and mode-converted waves on imaging. It is particularly important that the reflecting inhomogeneities in the ground be located accurately, regardless of the aperture angle of the radar antenna or of the sound. In the final method step, in the processed volume range, the video signal is formed and the result displayed in any desired layer planes and layer directions.

In a special embodiment, in reconstruction using the principle of the synthetic aperture, a special variation on signal evaluation is specified, namely a value that is proportional to the pulse energy. Note that in the known SAFT algorithms for each volume element, the signal intensity is summed at the corresponding point in time at each test head position. Improvements in the resolution and signal/noise interval however are advantageously achieved by virtue of the fact that a value proportional to the pulse energy is evaluated. According to the invention, the square of the ultrasound intensity is formed for each volume element for this purpose, and this is integrated by the expected application point of the echo for the entire pulse duration. Since the pulse lengths at a given point are not known exactly because of the frequency-dependent attenuation of sound and the weakening of microwaves, in a preliminary simulation at a reflector whose volume is known, the pulse width advantageously is varied in the evaluation and the correct value for the respective depth range is determined.

Reference Numbers 1 data acquisition by means of ultrasound
2 data acquisition by means of ground radar
3 memory
4 imaging method
5 structural representation taking into account the density and differences in the speed of sound
6 structural representation taking into account differences in dielectric constants
7 image comparison
8 image processing
9 representation
10 concrete wall
12 test head transmitter
14 receiver
16 combined test head
18 surface
20 housing
22 ring
24 hose
26 radar antenna
28 scanning interval

What is claimed is:

1. A method for testing and monitoring a structure by nondestructive three-dimensional detection of structural elements in said structure, said method comprising the steps of:
  scanning an area of the structure to be investigated with ultrasound;
  recording high-frequency, travel-time dependent ultrasound scan data for individual scanned points within the scanned area,
  imaging a three-dimensional image of the scanned area from the recorded ultrasound scan data,
  providing an image representation of the area as a function of density changes and sound speed differences,
  scanning the area to be investigated with radar,
  creating a structural representation of the scanned area based on data acquired in the radar scan,
  providing an image representation of the area as a function of dielectric constants, and
  calibrating the three-dimensional image of the scanned area determined from the ultrasound scan with the structural representation of the scanned area based on the radar scan by varying radar and ultrasound parameters to thereby provide testing and monitoring of the structure.

2. A method according to claim 1, wherein said structure is made of concrete.

3. A method according to claim 1, wherein the calibration is performed based on structural elements present in both the three-dimensional ultrasound image and in the radar structural representation.

4. A method according to claim 1, wherein the three-dimensional ultrasound image and the radar structural representation are derived independently of each other, and the dimensional scales of the independently derived three-dimensional ultrasound image and radar structural image are adapted to each other by means of structural elements present in both.

5. A method according to claim 1, wherein localized volumes of the respective three-dimensional ultrasound image and radar structural representation are calibrated based on structural elements present in both an independently derived ultrasound image and radar structural representation.

6. A method according to claim 1, wherein the scanning using ultrasound and the scanning using radar are performed at the same positions.

7. A method according to claim 1, wherein the scanning using ultrasound and the scanning using radar are performed at different positions, and wherein the relative positions of all the scanning points of each scan with respect to one another are known and recorded.

8. A method according to claim 1, wherein said ultrasonic imaging is performed using a synthetic aperture focusing technique, and respective volumes are calculated for the three-dimensional ultrasound image and the radar structural representation.

9. A method according to claim 1, wherein a three-dimensional volume is determined from both the data acquired using ultrasound and the data acquired using radar.

10. A method according to claim 8, wherein by means of the three-dimensional SAFT ultrasound imaging method, a common volume range is generated.

11. A method according to claim 8, wherein layer thicknesses of structural layers can be displayed in directions that can be specified in advance.

12. A method according to claim 11, wherein layer thicknesses both parallel to a measurement surface and orthogonal to the measurement surface are displayed.

13. A method according to claim 1, further comprising improving the signal/noise ratio by integration during a volume reconstruction.

14. A method according to claim 1, further comprising forming the square of ultrasound intensity for each of a formed volume element, and then integrating by an anticipated point of application of an echo for an entire pulse duration.

15. A method according to claim 1, wherein said method comprises acquiring data from respective sectional planes of the area to be investigated, and relating the acquired data from the respective sectional planes to each other.

16. A method according to claim 1, wherein said method comprises matching corresponding positions of the respective scans, and quantitatively analyzing the volume of a scanned structure.

17. A method according to claim 1, further comprising determining an identity of an unknown material based on measured dielectric constant and moisture distribution.

18. A method according to claim 1, further comprising determining a pulse length value which is correct for a respective depth in a preliminary simulation by varying a scan pulse width of a scan at a known reflector present in the structure at said depth until a measured result is obtained which corresponds in dimension to the known reflector.

19. A method according to claim 1, further comprising at least partially compensating for at least one of frequency-dependent sound attenuation and microwave attenuation.

20. A method according to claim 1, wherein an ultrasonic sensor used for the ultrasonic scanning and a radar sensor used for the radar scanning are spaced apart a distance equal to a scanning interval or to a multiple of the scanning interval of the ultrasound and radar scans.

21. The method according to claim 1 further comprising the steps of using a three-dimensional algorithm to assign amplitudes to each sample point of a recorded signal at each position point of sensors of said ultrasound as well as assign amplitudes to each spatial point of said recorded signal at each position point of each sensor of said radar; and summing said amplitudes to provide said three-dimensional image.

* * * * *